United States Patent [19]

O'Mahony et al.

[11] Patent Number: 5,596,984
[45] Date of Patent: Jan. 28, 1997

[54] LUNG VENTILATOR SAFETY CIRCUIT

[75] Inventors: John J. O'Mahony, Galway, Ireland; Floyd R. Farnham, III, Encinitas, Calif.

[73] Assignee: Puritan-Bennett Corporation, Overland Park, Kans.

[21] Appl. No.: 304,047

[22] Filed: Sep. 12, 1994

[51] Int. Cl.$^6$ ........................................... A61M 16/00
[52] U.S. Cl. ........................ 128/205.24; 128/204.21; 128/204.18
[58] Field of Search ..................... 128/204.18, 204.21, 128/204.23, 204.26, 205.23, 205.24

[56]  References Cited

U.S. PATENT DOCUMENTS

| | | | |
|---|---|---|---|
| 3,844,280 | 10/1974 | Smythe | 128/205.13 |
| 3,961,627 | 6/1976 | Ernst et al. | 128/204.21 |
| 4,393,869 | 7/1983 | Boyarsky et al. | 128/204.18 |
| 4,587,967 | 5/1986 | Chu et al. | 128/204.21 |
| 4,971,049 | 11/1990 | Rotariu et al. | 128/204.21 |
| 5,099,837 | 3/1992 | Russel et al. | 128/204.18 |
| 5,107,830 | 4/1992 | Younes | 128/204.18 |
| 5,265,594 | 11/1993 | Olsson et al. | 128/204.18 |
| 5,273,031 | 12/1993 | Olsson et al. | 128/204.18 |
| 5,303,698 | 4/1994 | Tobia et al. | 128/204.21 |
| 5,314,402 | 5/1994 | Foote et al. | 128/202.11 |
| 5,368,019 | 11/1994 | Latorraca | 128/204.18 |
| 5,419,768 | 5/1995 | Kayser | 128/205.24 |
| 5,433,193 | 7/1995 | Sanders et al. | 128/204.18 |

FOREIGN PATENT DOCUMENTS

| | | | |
|---|---|---|---|
| 1319175 | 6/1993 | Canada . | |
| 0080155 | 6/1983 | European Pat. Off. | 128/204.21 |
| 0146220 | 11/1983 | European Pat. Off. . | |
| 2573658A1 | 11/1984 | France . | |

OTHER PUBLICATIONS

Younes, et al., "Proportional Assist Ventilation"; Am Rev Respir Dis 1992; 145: 121–129.

Younes, et al., "An apparatus for altering the mechanical load of the respiratory system," J. Appl. Physiol. 62(6):2491–2499, 1987.

*Primary Examiner*—V. Millin
*Assistant Examiner*—William J. Deane, Jr.
*Attorney, Agent, or Firm*—Fulwider Patton Lee & Utecht

[57] ABSTRACT

The lung ventilator safety valve circuit includes a normally open, pulse width modulated solenoid safety valve connected to a patient airway of a ventilator system. A pressure sensor monitors pressure in the patient airway, and a control unit maintains the safety valve closed when the pressure is not excessive. The safety valve is opened when the sensed pressure equals or exceeds a maximum airway pressure threshold that can be set by an operator, or in the event of a power failure.

7 Claims, 1 Drawing Sheet

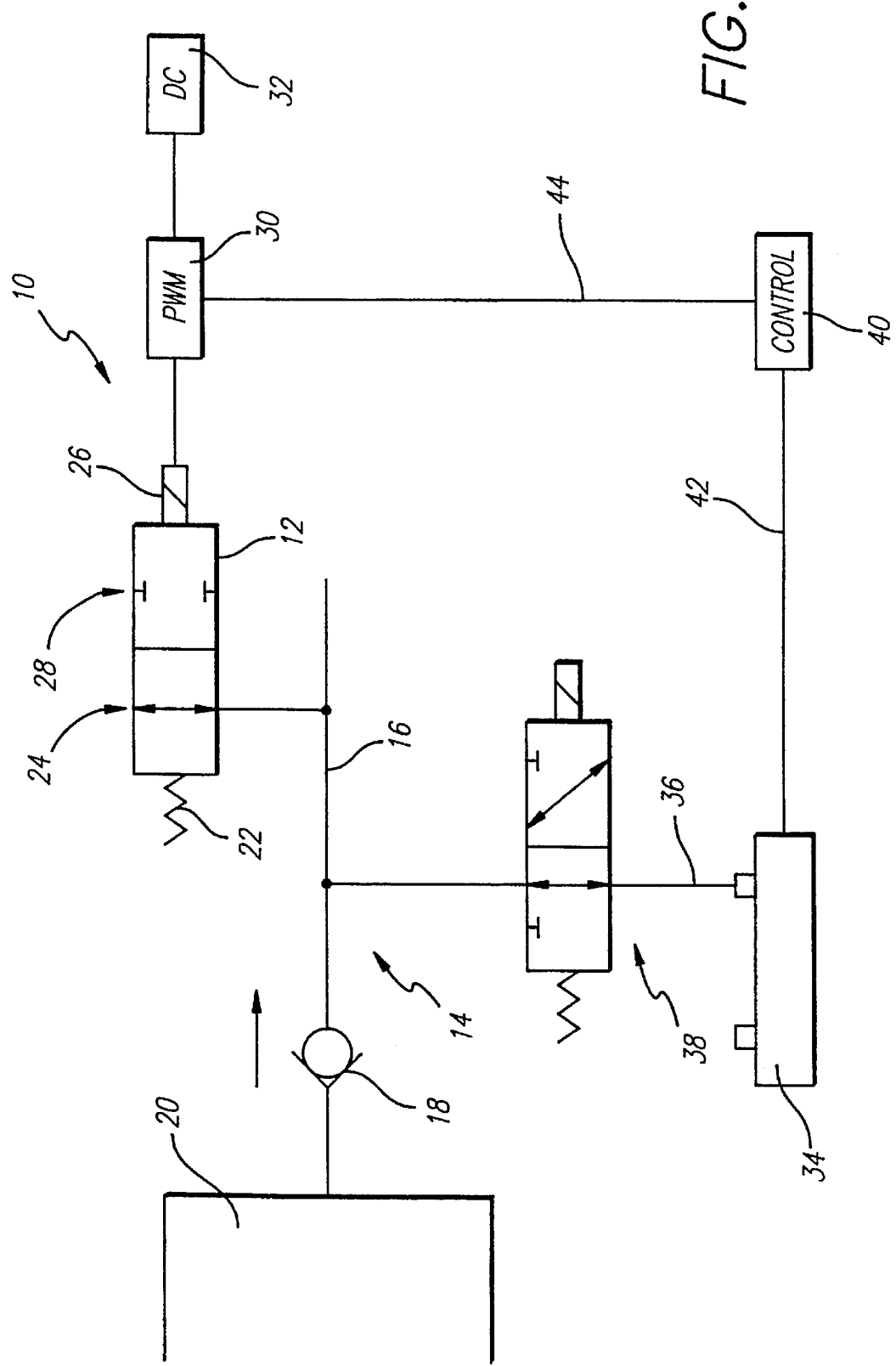

LUNG VENTILATOR SAFETY CIRCUIT

BACKGROUND OF THE INVENTION

1. Field of the Invention

This invention relates generally to breathing ventilators, and more particularly relates to a programmable safety circuit for a lung ventilator that provides ventilation pressure relief when ventilation pressure exceeds a set maximum pressure.

2. Description of Related Art

Medical ventilators are generally designed to ventilate a patient's lungs with breathing gas to assist a patient in breathing when the patient is somehow unable to adequately breath without assistance. Pressure assistance can be instituted, for example, when the patient has already begun an inspiratory effort. With such a system, it is desirable to immediately increase the pressure after a breath is initiated in order to reach a target pressure. This rise in pressure causes flow to be initiated in the patient airway which supplies breathing gas to the patient's lungs. Conventional pressure controlled ventilator systems typically implement a gas flow control strategy of terminating or reducing breathing gas flow when the target pressure is reached, to limit patient airway pressure.

However, such a control strategy can result in over-pressurization of the patient's lungs, particularly when high pressure gasses are used for blending the breathing gas mixture. When the over-pressurization is sustained, the patient's lungs can be subjected to excessive pressure for an entire inspiration portion of a breath cycle. When this occurs, the possibility exists that the patient will be harmed by a higher than desirable pressure in the lungs. Such overpressure can, for example, rupture sutures or blood vessels of a patient that has recently undergone thoracic or abdominal surgery. Similarly, frail or infirm patients, such asthmatic or emphysemic patients, can also be harmed if airway pressure is excessive.

Conventional ventilators have also typically limited ventilator pressure to a maximum by a pressure relief valve or safety valve with a fixed maximum rated pressure. However, such systems do not provide for a setting of the desired maximum pressure, which may be considerably lowered for infants or intensive care patients. Patient airway pressure can be also be actively controlled by an exhalation valve, although in some ventilators such exhalation valves can be simply closed during inspiration in order to achieve a set maximum ventilator pressure, so that it is possible for excessive pressure buildup to occur during inspiration pressure assistance. Ventilator system malfunctions can also result in overpressurization in the event of failure of a high pressure gas delivery valve controlling introduction of one of the breathing gas components into a high pressure blender.

For example, one known piston based lung ventilator utilizes a rolling-seal piston of low inertia and low frictional resistance for delivery of breathing gas, which is mixed in the piston chamber. For mixing of the breathing gas in the piston chamber, the piston chamber has an inlet connected to the airway of the patient, and a one-way valve allows air to enter the piston chamber during the exhalation phase of the respiratory cycle. Another gas inlet to the piston chamber, controlled by a solenoid valve, allows introduction of a desired gas mixture into the piston chamber. A valve for introducing the gas mixture is opened during expiration as the piston reciprocates to a baseline position. The oxygen content of the inspired gas can also be enriched by admitting a continuous flow of oxygen into the piston chamber through another inlet. However, the gases mixed in the breathing gas are supplied at high pressure. If a valve controlling the introduction of high pressure oxygen or air fails, breathing gas can be provided to a patient at an excessive pressure.

It would be therefore be desirable to provide a programmable lung ventilator safety circuit useful with virtually any type of ventilator delivering breathing gas under pressure, to limit the ventilator airway pressure to a maximum pressure appropriate for each particular patient, so that even if the ventilator should fail for some reason to provide ventilator pressure below an acceptable maximum, breathing gas will not be provided to a patient at an excessive pressure. The present invention meets these needs.

SUMMARY OF THE INVENTION

Briefly, and in general terms, the present invention provides for a lung ventilator safety valve circuit that can be programmed to open at any desired pressure, and a method for relieving pressure in a patient airway of a ventilator system incorporating the safety valve circuit. The safety valve circuit allows ventilation pressure relief that is appropriate for the desired maximum pressure that is set. The safety circuit includes a normally open, pulse width modulated solenoid valve that automatically opens in the event of a power failure, and permits low power consumption and a low operating temperature for the valve.

The present invention accordingly provides for a lung ventilator safety valve apparatus for relieving pressure in a patient airway of a ventilator system, that includes a safety valve connected to a patient airway of a ventilator system. The safety valve has a normally open position when no power is applied to the valve for venting pressure from the patient airway and a closed position when power is applied to the valve. In a preferred aspect of the invention, the safety valve is a pulse width actuated solenoid valve biased to the normally open position. Pressure sensor means are connected to the patient airway for monitoring pressure in the patient airway and for generating a pressure signal indicative of sensed pressure in the patient airway. Valve control means are also connected to the pressure sensor means for controlling the operation of the safety valve responsive to the pressure signal. The valve control means preferably includes means for setting a maximum airway pressure threshold, and means for comparing the sensed pressure in the patient airway with the maximum airway pressure threshold. The valve control means preferably generates a valve close signal until the sensed pressure in the patient airway is equal to or greater than the maximum airway pressure threshold, at which time the valve control means generates a valve open signal. Valve switching means are also preferably provided for receiving the valve close signal and the valve open signal for switching the safety valve between the closed position and the open position in response to the valve close signal and the valve open signal, respectively. In a preferred aspect of the invention, the valve switching means comprises a power source for providing cyclical pulses of power for operating the solenoid valve, and pulse width modulation means for modulating the duration of the pulses for moving the safety valve between the closed position and the open position.

The invention also provides for a method for relieving pressure in a patient airway of a ventilator system including a safety valve connected to a patient airway of a ventilator system and having a normally open position venting pressure from the patient airway and a closed position. In the method, pressure is monitored in the patient airway and a pressure signal indicative of sensed pressure in the patient airway is generated. A maximum airway pressure threshold is set, and the sensed pressure in the patient airway based upon the pressure signal is compared with the maximum airway pressure threshold. A valve open signal is generated when the sensed pressure in the patient airway is equal or greater to the maximum airway pressure. The safety valve is then switched to the open position in response to the valve open signal. In one preferred aspect of the method, where the safety valve is a pulse width actuated solenoid valve biased to the first normally open position, the step of switching the safety valve preferably comprises providing cyclical pulses of power for operating the solenoid valve, and modulating the duration of the pulses for moving the safety valve to the second, closed position.

These and other aspects and advantages of the invention will become apparent from the following detailed description, and the accompanying drawing, which illustrates by way of example the features of the invention.

BRIEF DESCRIPTION OF THE DRAWINGS

FIG. 1 is a schematic diagram of the lung ventilator safety valve circuit of the invention.

DETAILED DESCRIPTION OF A PREFERRED EMBODIMENT

Over-pressurization of a patient's lungs can be particularly harmful to pediatric or adult critical care patients. While conventional ventilators typically limit patient airway pressure by a pressure relief valve or safety valve with a fixed maximum rated pressure, such systems do not provide for a setting of a desired maximum pressure, which may be considerably lowered for infants or intensive care patients. It is possible for excessive pressure buildup to occur during inspiration pressure assistance in many types of ventilator systems delivering pressurized breathing gas, such as bellows, piston, and pressure solenoid type ventilators, for example, and the like.

As is illustrated in the drawings, the invention is embodied in a lung ventilator safety valve circuit 10 for relieving pressure in a patient airway of a ventilator system, such as a ventilator system providing pressure supported breaths, and having a limited air supply. With reference to FIG. 1, illustrating the apparatus of the invention in combination with an exemplary piston type ventilator, the lung ventilator safety valve circuit of the invention includes a safety valve 12 connected to a patient airway 14 of a ventilator system, such as the inspiratory line 16 connected through a check valve 18 to a piston cylinder 20 of the ventilator. The safety valve is preferably a two position spring loaded solenoid valve, in which the spring 22 of the solenoid valve urges the valve to a normally open position 24 venting pressure from the patient airway. When activated, the coil 26 of the solenoid urges the valve to a closed position 28, allowing the inspiratory line to deliver pressure support without diminution from the piston cylinder of the ventilator. The safety valve is preferably a pulse width modulated type of spring biased DC solenoid valve actuated by pulse width modulated signal from a pulse width modulator 30, which varies the duration of the power signal provided by a power source 32, such as a DC power supply. Alternatively, the safety valve can be controlled by amplitude modulation of an AC type solenoid, or by analog control of the base of a power transistor which would control the current available to the solenoid.

With the DC operated solenoid, in order to gain power consumption control, which in turn provides force control, the solenoid is preferably provided with a pulse width modulated signal with a high enough frequency to ensure that the solenoid was not given enough time to retract. Since the power consumption of the solenoid is controlled, the safety valve can be utilized as a relief valve. When the solenoid is closed, with a given power consumption, the solenoid will generate a specific force. Once this relationship is determined for the specific solenoid, by varying the power consumption of the solenoid, it is possible to program the valve to open like a relief valve at a given pressure. The safety valve may also be used in conjunction with a pressure transducer which would be used to determine if airway pressure had exceeded the high pressure limit set by the operator. If the airway pressure exceeds the high pressure threshold, power can be cut to the safety valve, causing the valve to open. While pulse width modulation is not necessary for this strategy, pulse width modulation can reduce power consumption of the solenoid. Solenoid valves normally require a higher power consumption to close than to remain closed, as the closing force is normally greater than the holding force. By pulse width modulation control of power consumption of the solenoid, power required by the solenoid can be reduced once the solenoid is closed, without affecting the sealing properties of the solenoid valve.

A pressure transducer 34 is preferably connected through a conduit 36 and a valve 38 to the inspiratory line of the patient airway for monitoring pressure in the patient airway. The pressure transducer generates a pressure signal indicative of sensed pressure in the patient airway that is received by a control unit 40 via line 42. The control unit is connected to the pulse width modulator via line 44 for controlling duration of the power signal pulses to the solenoid valve. The control unit also preferably includes means, such as a dial or keyboard, for example, for setting a desired maximum airway pressure threshold appropriate for a patient receiving breath assistance from the ventilator. The control unit includes means for comparing the sensed pressure in the patient airway, indicated by the pressure signal, with the maximum airway pressure threshold, which can be set by an operator, or which can be under program control set by an operator, for example. In one preferred embodiment, the means for setting a maximum airway pressure threshold is programmable, so that the safety valve circuit can be made to be compatible with various types of ventilation strategies, such as APRV (Airway Pressure Relief Ventilation) for example, in which two baseline pressure levels are cycled at a fixed rate in time with a constant flow rate, and a programmed cycle of patient airway pressure is superimposed over the preset baseline pressures. When the sensed pressure in the patient airway is equal to or exceeds the maximum airway pressure, the control unit reduces the duration of the pulsed power signal, to switch the solenoid valve to its normally open position, to vent excess pressure in the patient airway to the atmosphere.

In operation of the ventilator safety valve circuit, pressure is monitored in the patient airway by the pressure transducer, to provide a pressure signal indicative of the sensed pressure in the patient airway. A maximum airway pressure threshold is set in the control unit by an operator. The control unit receives the pressure signal from the pressure transducer and compares the sensed pressure in the patient airway with the maximum airway pressure threshold. The control unit generates a valve open signal when the sensed pressure in the patient airway is equal or greater to the maximum airway pressure, and the safety valve is then switched to the open position in response to the valve open signal. In one preferred aspect of the method, where the safety valve is a pulse width actuated solenoid valve biased to the first normally open position, the step of switching the safety valve preferably comprises providing cyclical pulses of power for operating the solenoid valve, and modulating the duration of the pulses for moving the safety valve to the second, closed position.

It has thus been demonstrated that the invention provides for a programmable lung ventilator safety circuit and a method for operating the circuit, in which the safety circuit can be set to open at a pressure appropriate for the patient receiving breath support, to provide ventilation pressure relief when airway pressure reaches the set maximum pressure. The normally open, pulse width modulated solenoid safety valve opens in the event of a power failure, and the pulse width modulation of operation of the valve permits low valve power consumption and a low operating temperature.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A lung ventilator safety valve apparatus for relieving pressure in a patient airway of a ventilator system, comprising:

a safety valve connected to a patient airway of a ventilator system, said safety valve having a normally open position venting pressure from said patient airway and a closed position;

pressure sensor means connected to said patient airway for monitoring pressure in said patient airway and for generating a pressure signal indicative of sensed pressure in said patient airway;

valve control means connected to said safety valve for controlling operation of said safety valve, and connected to said pressure sensor means for receiving said pressure signal, said valve control means including means for setting a maximum airway pressure threshold, means for comparing said sensed pressure in said patient airway with said maximum airway pressure threshold, and means for generating a valve open signal when said sensed pressure in said patient airway is equal to or greater than said maximum airway pressure; and valve switching means connected to said valve control means for receiving said valve open signal for switching said safety valve to said open position in response to said valve open signal.

2. The lung ventilator safety valve apparatus of claim 1, wherein said safety valve comprises a pulse width actuated solenoid valve biased to said normally open position.

3. The lung ventilator safety valve apparatus of claim 1, wherein said means for setting a maximum airway pressure threshold comprises a keyboard.

4. The lung ventilator safety valve apparatus of claim 2, wherein said valve switching means comprises a pulse power source for providing cyclical pulses of power for operating said solenoid valve, and pulse width modulation means for modulating the duration of said pulses for moving said safety valve to said closed position.

5. The lung ventilator safety valve apparatus of claim 1, wherein said means for setting a maximum airway pressure threshold comprises a dial.

6. A method for relieving pressure in a patient airway of a ventilator system, said ventilator system including a safety valve connected to a patient airway of a ventilator system, said safety valve having a normally open position venting pressure from said patient airway and a closed position, the steps of the method comprising:

monitoring pressure in said patient airway and generating a pressure signal indicative of sensed pressure in said patient airway;

setting a maximum airway pressure threshold, comparing said sensed pressure in said patient airway based upon said pressure signal with said maximum airway pressure threshold, and generating a valve open signal when said sensed pressure in said patient airway is equal to or greater than said maximum airway pressure; and switching said safety valve to said open position in response to said valve open signal.

7. The method of claim 6, wherein said safety valve is a pulse width actuated solenoid valve biased to said first normally open position, and said step of switching said safety valve comprises providing cyclical pulses of power for operating said solenoid valve, and modulating the duration of said pulses for moving said safety valve to said second, closed position.

\* \* \* \* \*